United States Patent [19]
Penney

[11] Patent Number: 5,980,913
[45] Date of Patent: Nov. 9, 1999

[54] PEPTIDES HAVING IMMUNOMODULATORY ACTIVITY

[75] Inventor: Christopher L. Penney, Quebec, Canada

[73] Assignee: Biochem Pharma, Inc., Quebec, Canada

[21] Appl. No.: 08/860,008

[22] PCT Filed: Dec. 15, 1995

[86] PCT No.: PCT/CA95/00703

§ 371 Date: Jun. 19, 1997

§ 102(e) Date: Jun. 19, 1997

[87] PCT Pub. No.: WO96/19494

PCT Pub. Date: Jun. 27, 1996

[30] Foreign Application Priority Data

Dec. 19, 1994 [GB] United Kingdom .................... 9425582

[51] Int. Cl.$^6$ .......................... A61K 38/04; A61K 45/00
[52] U.S. Cl. ......................................... 424/278.1; 530/330
[58] Field of Search .............................. 424/199.1, 278.1; 530/330

[56] References Cited

FOREIGN PATENT DOCUMENTS

| | | |
|---|---|---|
| 342 962 | 11/1989 | European Pat. Off. . |
| A 0 342 962 | 11/1989 | European Pat. Off. . |
| 517 464 A1 | 12/1992 | European Pat. Off. . |
| A 0 517 464 | 12/1992 | European Pat. Off. . |
| 526 192 A2 | 2/1993 | European Pat. Off. . |
| A0 526 192 | 2/1993 | European Pat. Off. . |
| 89/03430 | 4/1989 | WIPO . |
| WO A 89 03430 | 4/1989 | WIPO . |
| 92/09628 | 6/1992 | WIPO . |
| 92/10511 | 6/1992 | WIPO . |
| WOA92 09628 | 6/1992 | WIPO . |
| WOA92 10511 | 6/1992 | WIPO . |

OTHER PUBLICATIONS

Matsuda et al., "Manufacture of peptides by hydrolysis of actin–series proteins, and activity as angiotensin 1–converting enzyme inhibitors" Abstract Jpn. Kakai Tottyo Koho, 6 pp. CODEN: JKXXAF.

Birr et al., "Propeptides of proalbumin and their use" Abstract Ger. Offen., 24pp. CODEN: GWXXBX May 5, 1983.

Database WPI, Sect.ch.week 9345, Derwent Pub. ClassB04, AN93–357193.

H. Niedrich, "Synthesis of some tetrapeptide analogs of the eledoisin sequence KDAF" pp.3136.

J. Prakt Chem. vol. 35, No. 3–4, 1967pp.213–224.

I.Z. Siemion E.A., "Suppression of tuftsin activity by the partial sequences of adenovirus type 2 proteins", see pp. 300–306, vol. 41, 1993 International Journal of Peptide and Protein Research.

N.A. Leone E.A. "Characterisation of an epitope", pp. 327–330, vol. 335, No. 3 Dec. 1993, FEBS Letters.

Siemion, et al., "Suppression of tuftsin activity . . . ", Int. J. Peptide Protein Res. 41 (1993), 300–306.

Semni, E., "New angiotensin convert enzyme . . . ", CA 67 (1967), 3136.

Leone, et al., "Characterisation of an epitope recognised . . . ", FEBS 335, 3 (1993), 327–330.

*Primary Examiner*—Donna Wortman
*Assistant Examiner*—Brenda G. Brumback
*Attorney, Agent, or Firm*—Nixon & Vanderhye

[57] ABSTRACT

The present invention relates to peptides having an immunomodulatory activity. The present invention is concerned with the tetrapeptide H-Lys-Asn-Pro-Tyr-OH (SEQ.ID NO:1) and analogues thereof as immunomodulators. The present invention also includes the use of such peptides as vaccine adjuvant.

19 Claims, 2 Drawing Sheets

5,980,913

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (v) FRAGMENT TYPE: linear (xi) SEQUENCE DESCRIPTION: SEQ ID NO:1:

Lys Asn Pro Tyr
1

(2) INFORMATION FOR SEQ ID NO:2:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (v) FRAGMENT TYPE: linear (xi) SEQUENCE DESCRIPTION: SEQ ID NO:2:

Lys Asn Gly Tyr
1

(2) INFORMATION FOR SEQ ID NO:3:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (v) FRAGMENT TYPE: linear (xi) SEQUENCE DESCRIPTION: SEQ ID NO:3:

Lys Asn Pro Phe
1

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (v) FRAGMENT TYPE: linear (xi) SEQUENCE DESCRIPTION: SEQ ID NO:4:

Lys Gln Pro Tyr
1

(2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (v) FRAGMENT TYPE: linear (xi) SEQUENCE DESCRIPTION: SEQ ID NO:5:

Gly Lys Asn Pro Tyr
1               5

(2) INFORMATION FOR SEQ ID NO:6:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (v) FRAGMENT TYPE: linear (xi) SEQUENCE DESCRIPTION: SEQ ID NO:6:

Gly Asn Pro Tyr

PEPTIDES HAVING IMMUNOMODULATORY ACTIVITY

FIELD OF THE INVENTION

The present invention relates to peptides having an immunomodulatory activity. In particular, the present invention relates to peptides which stimulate the immune system in animals, including humans. The present invention is concerned with the tetrapeptide H-Lys-Asn-Pro-Tyr-OH (SEQ ID NO:1) and analogues thereof as immunomodulators.

The present invention also includes compositions containing such immunomodulatory peptides and the use of such peptides and compositions as immunomodulators.

The present invention also includes the use of such peptides as a vaccine adjuvant.

BACKGROUND OF THE INVENTION

The primary function of the immune system relates to the protection of the body from disease. The immune system protects against not only those diseases which result from an attack by bacteria, virus, and other pathogens, but also cancer, as well as disease states which result from immune imbalance; opportunistic infections, or autoimmune disorders.

In a number of diseases or other pathological conditions, the immune system response of an animal or human is depressed. As a result, the subject becomes more susceptible to malignancies, or pathological infections against which a normal immune system would have protected the subject. Some conditions which depress the immune system include acquired immune deficiency syndrome (AIDS), chronic infection, chemotherapy, trauma of surgery, and aging.

Modulation of the immune system through pharmaceutically induced stimulation or suppression offers an important approach to the control of disease. Compounds which non-specifically stimulate the immune system are of potentially significant medicinal importance and have been the object of lengthy research efforts. Often, the research results show that immunomodulating compounds are either weak immunostimulants, and therefore not very effective, or potent immunostimulants and, therefore, effective but toxic by virtue of this potent immunostimulating activity.

Among the many classes of compounds which non-specifically stimulate the immune system are a number of naturally occurring peptides or fragments thereof. One such fragment is Imreg, a tripeptide of the general sequence Tyr-Gly-Gly disclosed in U.S. Pat. No. 4,699,898 issued Oct. 13, 1987. This patent does not disclose the sequence of the peptides of the present invention. Imreg can be isolated from human leukocytes. It is a thymomimetic but possesses weak potency. (A. Arthur Gottlieb, Int.J.Immunopharm.Vol.13, Suppl.1, p.29–32 (1991)).

Another fragment of a naturally occurring peptide is the tetrapeptide Tuftsin and its close analogue Rigin. These peptides have the respective sequences Thr-Lys-Pro-Arg and Gly-Gln-Pro-Arg. Analogues of tuftsin can be found, for example, in Biondi et al., "Synthesis of glycosylated tuftsins and tuftsin-containing IgG fragment undecapeptide", Int.J.Peptide Protein Res. 37, 1991, p.112–121, and Verdini et al., "Immunostimulation by a partially modified retro-inverso-Tuftsin analogue containing $Thr^1\psi[NHCO](R,S) Lys^2$ modification", J.Med.Chem., 1991 34, p.3372–3379. These publications do not disclose peptides with the sequence of the present invention. Tuftsin and rigin are both fragments of IgG and are found within the heavy chain of leukokinin. Tuftsin is a well-known macrophage activator and is known to stimulate NK cell activity. However, it is unstable in plasma which may strongly reduce its stimulating effects on the immune system.

Another fragment of a naturally occurring peptide known to have immunomodulating effects is thymopentin. (Audhya et al., "Contrasting biological activities of thymopoietin and splenin, two closely related polypeptide products of thymus and spleen", Proc.Natl.Acad.Sci.USA, 81,p.2847–2849, 1984; U.S. Pat. No. 5,218,089 issued Jun. 8, 1993; U.S. Pat. No. 5,091,510 issued Feb. 25, 1992). This pentapeptide has the sequence Arg-Lys-Asp-Val-Tyr. Thymopoietin is a 49 amino acid polypeptide thymus hormone. The pentapeptide is the smallest fragment of thymopoietinq which retains the immunological activity of the parent hormone. Thymopentin is a thymomimetic of weak potency. It induces phenotypic differentiation of T cells and increases Interleukin-2 production. Splenin, an analogue of thymopentin, affects both B and T cells. Splenin has the sequence Arg-Lys-Glu-Val-Tyr in bovine and Arg-Lys-Ala-Val-Tyr in humans. Another similar peptide is thymotrinan which has the sequence Arg-Lys-Asp. While these peptides also produce immunomodulating effects, they do not contain or disclose the sequence of the peptides of the present invention.

Another naturally occurring compound is Eisenin extracted from a brown marine algae. This tripeptide has the sequence pyroGlu-Gln-Ala. It was reported in Kojima et al., "Eisenin (L-pyroGlu-L-Gln-L-Ala), a new biological response modifier", Journal of Immunotherapy, 13, p.36–42, 1993 that Eisenin showed immunological activity augmenting natural cytotoxicity of peripheral blood lymphocytes (PBLs) in humans. The natural cytotoxicity augmented by Eisenin seems to be due mainly to NK cells.

One peptide named "LANT 6" has the sequence Lys-Asn-Pro-Tyr-Ile-Leu. LANT6 has been found in ganglion cells and is believed to play a role in neurotransmission between retina ganglion cells and their central target areas. LANT 6 possesses some sequence homology with neurotensin. Neurotensin analogues have been described as cerebral medicaments, antipsychotic agents, analgesics, and anphetamine antagonists. However, LANT 6 has not been reported to have immunomodulatory activity.

Furthermore, it is known in the peptide art, as noted in U.S. Pat. No. 4,426,324 "Immunopotentiating Peptides" issued Jan. 17, 1984, that deletion of even one amino acid from the sequence of a biologically active peptide can result in the loss of biological activity. Therefore, the inclusion of the sequence of the present invention in the sequence of LANT 6 for use as a neuropeptide does not indicate that a shorter sequence within LANT6 would be active as an immunomodulator.

It is well known that vaccines are important in the prophylaxis of disease. Vaccines operate by exposing a host animal to foreign material designed to activate the immune system to confer upon the host immunity against the material without exposing the host to the risk of disease. At the present time, about 20 vaccines have been developed for commercial use. Some of these vaccines are made by detoxification of the toxin produced by the microorganism, or a portion of that organism, or by isolation of a specific non-toxic portion of the organism. A well known example of the latter is the isolation of capsular polysaccharides from meningococcal and pneumococcal bacteria as the basis for a vaccine for bacterial meningitis and pneumonia. However, polysaccharide vaccines are poor immunogens which do not give rise to adequate amounts of protective antibodies in individuals with poorly developed or impaired immune systems. The latter includes young children, the elderly, or those with autoimmune diseases. Furthermore, the immune response which does occur is T-independent or non-memory which means the individual will not display an increased antibody response, with seroconversion, upon being given a booster injection. T-cell dependence is necessary for the induction of IgG antibodies and memory cells. Thus, upon seroconversion, both IgM and IgG antibodies are formed upon repeated injections of a vaccine. Furthermore, the magnitude of the antibody response increases with each injection of vaccine, when the response is T-dependent. The immunology of polysaccharide vaccines has been reviewed by Kennings et al, "The Polysaccharides" (Editor; GO Spinal), Volume 1, 291–329 (1982).

As regards adjuvants for commercial use, only aluminum and calcium salts are presently employed as adjuvants. However, aluminum and calcium salts are not potent adjuvants. Calcium salts have found only limited use. While aluminum salts have found more widespread use with other vaccines, little success has been reported with polysaccharide protein conjugate vaccines. In fact, it has been reported that aluminum hydroxide inhibits the antibody response to an *H. Influenzae* b polysaccharide-tetanus toxoid conjugate vaccine; J. B. Robbins, et al also observe the same suppression of the antibody response with aluminum hydroxide and a *S Typhi* polysaccharide—cholera toxin conjugate vaccine; J. Experimental Medicine, 166, 1510–1524 (1897). Furthermore, aluminum salts may provoke transient or chronic local granulomas at the site of injection; L. H. Collier in lancet, 1354–1367 (1987) states that the incidence and severity of reactions to tetanus toxoid vaccine depends upon the presence of aluminum adjuvants. The preparation of aluminum adjuvants is not always reproducible. Moreover, aluminum can alone stimulate the production of IgE antibodies which are responsible for mediating immediate hypersensitive reactions. This has been described by T. Matuhasi et al, J. Infectious Disease, 146, 192 (1982).

Attention has focused in recent years on the use of organic compounds as immunoadjuvants. Only a few organic compounds function in a manner similar to commercially acceptable aluminum salts; i.e. as a slow release vehicle or antigen (vaccine) depot whereby antigen is released over a relatively long period of time at the site of injection.

Examples of such organic compounds are organic surfactants and emulsifiers, such as Pluronics and Tetronics which are non-ionic block copolymers of polyoxyethylene and polyoxypropylene produced by BASF Corporation. Such a slow-release mechanism of adjuvanticity has long been accepted for human use since it reduces the possibility of overstimulating the immune system. Overstimulation of the immune system can lead to an autoimmune response such as would occur with the use of a potent immunostimulant, for example Freund's adjuvant. Thus, the slow release mechanism is the preferred mechanism.

While the majority of organic adjuvants have been shown to be potent immunostimulants, such highly active adjuvants tend to be toxic and therefore unacceptable for human use. Examples of known organic adjuvants which are potent immunostimulants are Freund's complete adjuvant and muramyl dipeptide. Both of these compounds are restricted to use in animal research because of toxicity considerations. Many of the organic adjuvants which mimic aluminum salts are more toxic than aluminum salts. For example, long chain alkyl amines described by D. Gall in Immunology, 11, 369–386 (1966) are reported to be toxic compounds which are generally disruptive to cell membrane structure.

SUMMARY OF THE INVENTION

The present invention includes peptides of the formula (I):

$$X-R_1-R_2-R_3-R_4-Y \qquad (I)$$

and pharmaceutically acceptable derivatives thereof, wherein;

X is selected from the group consisting of H, acetyl, and glycyl or a conservative substitution thereof.

$R_1$ is lysine or a conservative substitution thereof.

$R_2$ is asparagine or a conservative substitution thereof.

$R_3$ is proline or a conservative substitution thereof.

$R_4$ is tyrosine or a conservative substitution thereof.

Y is selected from the group consisting of OH, $NH_2$, and $OC_{1-6}$ alkyl.

In accordance with the present invention, there is provided peptides of formula (I) having an immunomodulatory activity.

In particular, the peptides of the present invention cause stimulation of the immune system in mammals including human.

In another aspect of the present invention, there is provided pharmaceutical compositions containing such immunomodulatory peptides of formula (I).

In a further aspect of the invention, there is provided the use of such peptides of formula (I) and compositions as izunomodulators, and, in particular, as immunostimulants.

In a further aspect of the invention, there is provided the use of such peptides of formula (I) and compositions for stimulating B-cells.

In a still further aspect of the invention, there is provided a peptide of formula (I) which acts as a control against tumor growth and viral infections.

Another aspect of the present invention is the use of the peptides of formula (I) or pharmaceutical preparations for the manufacture of a medicament for the treatment of immune deficiencies, in an amount effective to produce an immune response.

Another aspect of the invention is the method of treatment of a mammal, preferably a human, comprising the step of administering an effective amount peptide of formula I, a pharmaceutical composition, or a pharmaceutically acceptable derivative thereof for the treatment of immune deficiency and tumor growth.

In a still further aspect of the invention, there is provided a peptide of formula (I) which can function as an adjuvant in a vaccine.

In a still further aspect of the invention, there is provided a peptide of formula (I) which can function as an adjuvant in a vaccine composition.

Another aspect of the present invention is the use of the peptides of formula (I) or pharmaceutical acceptable derivative for the manufacture of a vaccine composition.

Another aspect of the invention is the method for the prophylaxis of a disease, in a mammal, preferably a human, comprising the step of administering a vaccine comprising a compound of formula I, or a pharmaceutical composition, or a pharmaceutically acceptable derivative thereof, in an amount effective to produce an immune response.

Figure 1A:
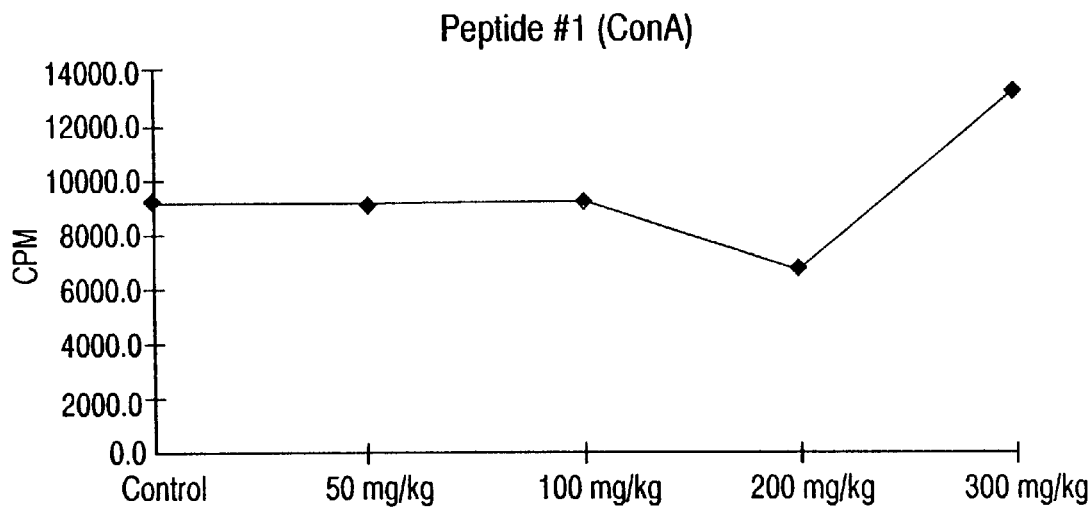
FIGS. 1A, 1B, 1C, and 1D show the activation of Ta and B cells in spleen in vivo/ex vivo by PEPTIDE #1 (SEQ. ID NO:1)

X is preferably selected from the group consisting of glycine; alanine; proline; glutamine; asparagine; serine;

threonine; and valine. X is more preferably selected from the group consisting of glycine; alanine; and valine. X is most preferably hydrogen.

$R_1$ is preferably selected from the group consisting of D or L-lysine; arginine; ornithine; and histidine. $R_1$ is more preferably D-lysine or L-lysine. $R_1$ is most preferably D-lysine.

$R_2$ is preferably selected from the group consisting of D or L-asparagine; alanine; proline; glutamine; serine; threonine; valine; and glycine. $R_2$ is more preferably selected from the group consisting of D or L-asparagine; and glutamine. $R_2$ is most preferably asparagine.

In an alternative preferred embodiment, $R_2$ is glutamine.

$R_3$ is preferably selected from the group consisting of glycine; D or L-Proline; alanine; asparagine; glutamine; serine; threonine; valine; and glycine. $R_3$ is more preferably glycine or D or L-Proline. $R_3$ is most preferably D-Proline.

$R_4$ is preferably selected from the group consisting of D or L-tyrosine; cysteine; serine; threonine; phenylalanine; tryptophan; and histidine. $R_4$ is more preferably selected from the group consisting of D or L-tyrosine; and phenylalanine. $R_4$ is most preferably tyrosine.

In an alternative preferred embodiment, $R_4$ is phenylalanine. Y is preferably OH or $NH_2$. Y is most preferably OH.

Preferred peptides of the present invention are listed as follows:
PEPTIDE #1 H-Lys-Asn-Pro-Tyr-OH (SEQ. ID NO:1);
PEPTIDE #2 H-Lys-Asn-Gly-Tyr-OH (SEQ. ID NO:2);
PEPTIDE #3 H-Lys-Asn-(D-Pro)-Tyr-OH (SEQ. ID NO:1);
PEPTIDE #4 H-Lys-Asn-Pro-Phe-OH (SEQ. ID NO:3);
PEPTIDE #5 H-(D-Lys)-Asn-Pro-Tyr-OH (SEQ. ID NO:1);
PEPTIDE #6 H-Lys-Gln-Pro-Tyr-OH (SEQ. ID NO:4);
PEPTIDE #7 B-Gly-Lys-Asn-Pro-Tyr-OH (SEQ. ID NO:5);
PEPTIDE #8 H-Gly-Asn-Pro-Tyr-OH (SEQ. ID NO:6);
PEPTIDE #9 H-(D-Lys)-Asn-Gly-Tyr-OH (SEQ. ID NO:2);
PEPTIDE #10 H-(D-Lys)-Gln-Pro-Tyr-OH (SEQ. ID NO:4); and
PEPTIDE #11 H-(D-Lys)-Asn-Pro-Phe-OH (SEQ. ID NO:3).

The more preferred compound of the present invention are
PEPTIDE #1 H-Lys-Asn-Pro-Tyr-OH; (SEQ. ID NO:1) and
PEPTIDE #5 H-(D-Lys)-Asn-Pro-Tyr-OH (SEQ. ID NO:1).

The most preferred compound of the present invention is PEPTIDE #5 H-(D-Lys)-Asn-Pro-Tyr-OH (SEQ. ID NO:1).

The term "amino acid" as employed herein includes and encompasses all of the naturally occurring amino acids, either in the D- or L-configuration if optically active, and the known non-native, synthetic, and modified amino acids, such as homocysteine, ornithine, norleucine and p-valine. A list of non natural amino acids may be found in "The Peptides", vol 5, 1983, Academic Press, Chapter 6 by D. C. Roberts and F. Vellaccio.

The term "conservative substitution" as employed herein refers to the amino acids in which the native sequence of the peptide of this invention have had conservative modifications or substitutions. These substitutions or modifications are those having a minimal influence on the secondary structure and hydropathic nature of the peptide. These include substitutions such as those described by Dayhoff in the Atlas of Protein Sequence and Structure 5, 1978 and in Argos in EMBO J. 8, 779–785, 1989. For example, amino acids belonging to one of the following groups represent conservative changes: ala, pro, gly, gln, asn, ser, thr, val; cys, ser, tyr, thr; val, ile, leu, met, ala, phe; lys, arg, orn, his; and phe, tyr, trp, his. The preferred substitutions also include substitutions of D-enantiomers for the corresponding L-amino acids.

The term "pharmaceutically acceptable derivative" as employed herein, includes any pharmaceutically acceptable salt, ester or amide, of a peptide of formula I or any other compound, analogue or derivative of formula 1 which, upon administration to the recipient, is capable of providing (directly or indirectly) a compound of formula I or an active metabolite or residue thereof.

The amino acids in the peptides of the present invention may be present in their natural L-configuration, unnatural D-configuration, or as a racemic mixture.

By the term "vaccine" is meant a preparation comprising killed microorganism, genitically modified microorganism, genitically engineered antigen (e.g. proteins, peptides, sugars, and/or glycopeptides), and/or naturally occuring antigen (e.g. proteins, peptides, sugars, and/or glycopeptides).

By the term "disease" is meant virus such as reovirus, rotavirus, orbivirus, retrovirus, lentivirus, picornavirus, papillomavirus, adenovirus, parvovirus, herpesvirus, poxvirus, hepadnavirus; and bacteria.

Virus can be selected from, but are not limited to the group consisting of influenza; hepatitis of type A, B, and C; human immune immunodefiency of type 1 and 2; chicken pox; cytomegalovirus; herpes virus of type 1 and 2; epstein barr; papilloma; and poliovirus of type I, II, and III.

Bacterium can be selected, but are not limited to the group consisting of tetanus; diptheria; pertussis; and meningococcus.

In a preferred embodiment, the adjuvant of this invention can be used in combination with the following vaccines: influenza; diphtheria, pertussis, tetanus(DPT); and meningitis.

There is also provided, in a further aspect of the invention a method for the prophylaxis of influenza, in a mammal, preferably a human, comprising the step of administering an influenza vaccine comprising a peptide of formula (I), a pharmaceutical composition, or a pharmaceutically acceptable derivative thereof, in an amount effective to produce an immune response.

There is also provided, in a further aspect of the invention a method for the prophylaxis of diphtheria, in a mammal, preferably a human, comprising the step of administering a diphtheria vaccine comprising a peptide of formula (I), a pharmaceutical composition, or a pharmaceutically acceptable derivative thereof, in an amount effective to produce an immune response.

There is also provided, in a further aspect of the invention a method for the prophylaxis of pertussis, in a mammal, preferably a human, comprising the step of administering a pertussis vaccine comprising a peptide of formula (I), a pharmaceutical composition, or a pharmaceutically acceptable derivative thereof, in an amount effective to produce an immune response.

There is also provided, in a further aspect of the invention a method for the prophylaxis of tetanus, in a mammal, preferably a human, comprising the step of administering a tetanus vaccine comprising a peptide of formula (I), a pharmaceutical composition, or a pharmaceutically acceptable derivative thereof, in an amount effective to produce an immune response.

There is also provided, in a further aspect of the invention a method for the prophylaxis of diphtheria, pertussis, and tetanus(DPT), in a mammal, preferably a human, comprising the step of administering a DPT vaccine comprising a peptide of formula (I), a pharmaceutical composition, or a pharmaceutically acceptable derivative thereof, in an amount effective to produce an immune response.

There is also provided, in a further aspect of the invention, a method for the prophylaxis of meningitis, in a mammal, preferably a human, comprising the step of administering a meningitis vaccine comprising a peptide of formula (I), a pharmaceutical composition, or a pharmaceutically acceptable derivative thereof, in an amount effective to produce an immune response.

It will be appreciated by those skilled in the art that the reference herein to treatment extends to prophylaxis as well as treatment of established infections or symptoms and therefore includes control of tumor outgrowth.

It will be further appreciated that the amount of a compound of the invention required for use in treatment will vary not only with the particular compound selected but also with the route of administration, the nature of the condition being treated, and the age and condition of the patient, and will be ultimately at the discretion of the attendant physician or veterinarian. In general, however, a suitable dose will be in the range from about 0.1 to about 750 mg/kg of body weight per day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, of active ingredient per unit dosage form.

Ideally the active ingredient should be administered to achieve peak plasma concentrations of the active compound. This may be achieved, for example, by the intravenous injection of a solution of the active ingredient, optionally in saline, or administered as a bolus. Desirable blood levels may be maintained by a continuous infusion or by intermitent infusions.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers thereof and, optionally, other therapeutic ingredients. The carrier(s) must be "acceptable" in the sense of being compatible with the other ingredients of the formulation and not deleterious to the recipient thereof.

Pharmaceutical formulations include those suitable for oral or parenteral (including intramuscular, sub-cutaneous and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

When desired, the above described formulations adapted to give sustained release of the active ingredient may be employed.

The peptides of the invention may also be used in combination with other therapeutically active agents, for example, other immunomodulators, antiviral agents, or anti-cancer agents.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

The individual components of such combinations may be administered either sequentially or simultaneously in separate or combined pharmaceutical formulations.

When the peptide of formula (I) or a pharmaceutically acceptable derivative thereof is used in combination with a second therapeutic agent, the dose of each compound may be either the same or differ from that when the compound is used alone. Appropriate doses will be readily appreciated by those skilled in the art.

It will be appreciated by those skilled in the art that the peptides of the present invention include all pharmaceutically acceptable derivatives and analogues thereof, as well as all isomers and enantiomers.

The vaccine compositions comprising the adjuvant of the invention can be prepared by physically mixing the adjuvant with the appropriate antigen under appropriate sterile conditions in accordance with known techniques to produce the adjuvanted compositions.

The amounts of the adjuvant and antigen needed to elicit an immune response in humans are interrelated, but are within the ranges generally employed in conventional vaccines. For example, the use of increasing amounts of adjuvant may suggest that decreasing amounts of antigen can be used, and vice versa. The preferred amount of adjuvant is 0.01 to 5 mg/ml of the composition, for example 0.05 mg/ml to 3 mg/ml, preferably 0.5 to 1.0 mg/ml. The preferred amount-of antigen is between about 1 to 100 micrograms/ml. Preferably about 5 to 45 micrograms/ml. The dosage will depend upon the host receiving the vaccine as well as factors such as the size, weight, and age of the host.

The vaccine compositions comprisimg the adjuvant of this invention may be formulated using techniques similar to those used for other pharmaceutical compositions. Thus, the adjuvant and antigen may be stored in lyophilized form and reconstituted in a physiologically acceptable vehicle to form a mixture prior to administration. Alternatively, the adjuvant and antigen may be stored in the vehicle. Preferred vehicles are sterile solutions, in particular, sterile buffer solutions, such as phosphate buffered saline. Any method of combining the adjuvant and the antigen in the vehicle such that improved immunological effectiveness of the composition relative to the individual components is appropriate.

The vehicle may contain preservatives or other known additives which are used to improve the shelf stability or the efficacy of the mixture. Suitable preservatives include, for example, thimerosal.

The vaccine compositions comprising the adjuvant of the invention may be administered by any convenient means. Preferred methods of administration include subcutaneous, intramuscular, intradermal, or by way of oral or nasal delivery. Alternatively, the mixture may be released from a biodiffusible implant. A single adminisration may be used. Alternatively a series of administrations may be made over the course of several days or weeks.

The peptides of formula (I) are prepared using standard solid phase peptide synthesis procedures. These procedures are well known to those persons skilled in the art. Such procedures are described in John M. Stewart and Janis D. Young, Solid *Phase Peptide Synthesis*, 2nd ed., (1984) Pierce Chemical Co., Illinois, U.S., which is incorporated herein by reference.

EXAMPLES

The peptides of formula I were synthesized and tested for immunological activity using the procedures outlined below.

9

The following examples are not intended to limit the invention in any way.

Example 1

Synthesis Protocol for the Peptides of the Invention abbreviations:
Pmoc: Fluorenylmethoxycarbonyl;
DMF: Dimethylformamide;
TFA: Trifluoroacetic acid;
HPLC: High performance liquid chromatography;
HOBT: 1-Hydroxybenzotriazole;
DCC: Dicylohexylcarbodiimide;
t-Bu: Tert-butyl;
Boc: Butoxycarbonyl;
Trt: Trityl.

The synthetic peptide was prepared using p-benzyloxybenzyl alcohol resin functionalized with the relevant C-terminal N-protected Fmoc-amino acid [Fmoc-Tyrosine(tBu)] and capped with benzyl chloride.

The remaining amino acids were all Fmoc protected at the alpha amino group and the following side chain protecting groups were utilized: Trt for asparagine and Boc for lysine.

Reagents used in the synthesis and cleavage were all ACS grade and used as such without further purification with the exception of the DMF used for the couplings which was dimethylamine free and TFA used in the cleavage which was of biograde purity. $H_2O$ and acetonitrile used for the purification were HPLC grade solvents. HCl used for salt exchange was of constant boiling grade.

Solid phase peptide synthesis was carried out manually. Resin loading was in the order of 0.53 meq/g and synthesis was carried out on a 10.59 mM scale.

Peptide condensation was carried out using 2 equivalents of Fmoc amino acid, HOBT and DCC in DMF (dimethylamine free) for 2 hours to overnight couplings at room temperature. Recouplings were carried out using 1 equivalent of reagents for 2–4 hours. Deprotection of the Fmoc moiety was accomplished using 20% (v/v) piperidine in DMF for 20–25 minutes at room temperature.

Cleavage of the peptide from the resin and removal of the side chain protecting groups (tBu, Boc, Trt) was carried out using a solution containing 55% TFA, 5% anisole and 40% dichloromethane for 90 minutes at room temperature under a nitrogen atmosphere. The resin was then washed successively using a solution of 20% TFA, 0.5% anisole and 79.5% dichloromethane. The combined filtrates were then evaporated under reduced pressure and the peptide was precipitated from diethyl ether, filtered, and lyophilized. The crude peptide was purified by HPLC on a preparative reversed phase column (Vydac® C18, 300 Å, 10–15 microns) using a flow rate of 160 ml/min with a gradient using $H_2O$ plus 0.06% TFA and acetonitrile plus 0.06% TFA in a 0–60% gradient over 60 minutes. Salt exchange to the HCl form was accomplished with the addition of an excess amount of HCl to the peptide in solution with successive lyophilization cycles.

The amino acid content of the purified tetrapeptide was determined by amino acid analysis after hydrolysis; 6N HCl, 110 C for 20 hours. A typical amino acid analysis is represented by the following:

Lys=1.02; Asp/Asn=0.99; Pro=1.07; Tyr=1.00.

Peptides synthesized by this method were tested in vitro and in vivo to assess imunomodulatory activity in the following manner.

Example 2

In Virto Stimulation of Immune Cell Subsets

The following abbreviations and definitions are used herein:
PHA—Phytohemagglutinin
ConA—Concanavalin A
LPS—Lipopolysaccharide
PMW—Pokeweed mitogen
PBS—Phosphate buffered saline 1. Cytotoxic T Lymphocytes (CTL) Mixed Lymphocyte Reaction (MLR) and Mitogenic Response Assays The protocols used are described in Hudson L., Haay F., *Pratical immunology*, $3^{rd}$ edition, Blackwell, Scientific publications, Oxford 1989, p. 158–162, and p.447.

Lymphocytes were isolated from C57BL/6 mice and DBA/2 mice in accordance to techniques well known in the art. Cell concentration was adjusted to $10\times10^6$ cell/ml for each assay. The cells isolated from DBA/2 mice were irradiated with 3000 Rads.

In a 6 well plate, each well was set up with:
1 ml of C57BL/6 cells;
1 ml of DBA/2 cells; and
1 ml of the drug at different concentrations (or IL-2 to 10 ng/ml final) in RPMI 10% supplemented.

The cells were incubated for five days at 37° C. in 5% $CO_2$, after which CTL and MLR assays were performed.

Results are presented in Table 1.

a) Cytotoxic T Lymphocytes (CTL)

P815 target cells were labelled with $Cr^{51}$ (0.1 mCi). After labelling, the cells were washed three times and resuspended to a concentration of $5\times10^4$ cells/ml in media. p T cells were then counted and diluted to obtain a concentration of $2.5\times10^6$ cells/ml, and then further diluted to obtain the following effector:target ratios:

50:1 ($2.5\times10^6$ cells/ml: $5\times10^4$ cell/ml)
25:1 ($1.25\times10^6$ cells/ml: $5\times10^4$ cells/ml)
12.5:1 ($0.625\times10^6$ cells/ml: $5\times10^4$ cells/ml).

100 µl of target cells+100 µl of CTLs were incubated for 4 hours. In parallel wells, 100 µl of target cells+100 µl of media were incubated for spntaneous release. After incubation, cells were centrifuged and 100 µl of supernatant was then counted using a gamma counter.

Results are expressed as % specific $^{51}Cr$ release=

$$\frac{ER - SR}{TR - SR} \times 100$$

where ER=experimental release,
SR=spontaneous releaase, and
TR=total release.

b) Mixed Lymphocyte Reaction (MLR)

Mixed lymphocyte reaction is an in vitro counterpart of the allograft rejection. Briefly, lymphocyte activation (mitotic response) is obtained when cells from two inbred strains or from two outbred individuals of any species are mixed in in vitro culture. To have a unidirectional response, the proliferation of either cell type may be blocked with X-ray irradiation or mitomycin C treatment. After 4 days incubation, $^3H$ thymidine uptake and cytotoxicity assays (CTL) were performed. The cells were then resuspended and 100 µl of cell suspension was deposited in each well of a 96 well plate. 1 µCi of tritiated thymidine was added for 6 hours. After incubation, the cells were then harvested and counted using a Microbeta counter.

c) Activation of T or B cells by Mitogenic Proliferation

A mitogenic lectin (mitogen) is a glycoprotein which binds and cross-links specific cells surface carbohydrate determinants, and will polyclonally stimulate lymphoid cells. Lymphocyte activation by either antigens or mitogens results in intracellular changes and the subsequent development into a lymphoblast. Mitogenic stimulation of lymphocytes in vitro is believed to mimic the series of events which occur in vivo following their stimulation by specific antigens. PHA and ConA; PWM and LPS mitogens can be used as a measurement of T cell and B cell activity, respectively. Briefly, the spleen mononuclear leukocytes from C57BL/6 mice are incubated in the presence or absence of mitogens with or without candidate drugs. After 72 hours or 5 days, $^3$H-thymidine incorporation is recorded as an indication of cell proliferation.

Lymphocytes were isolated from mice spleen or human blood in accordance to methods well known in the art. 100 $\mu$l of cell suspension of $2 \times 10^6$ cells/ml was added per well ($2 \times 10^5$ cells/well) and incubated in the presence of lectin at the following concentrations:

Human T cells:
  PHA=0.01% final concentration
  ConA=0.2 $\mu$g/ml
Human B cells:
  PWM=0.01 to 0.1 $\mu$g/ml
  LPS=10 $\mu$g/ml
Mouse T cells:
  PHA=0.01% to 0.001% final concentration
  ConA=1 to 2 $\mu$g/ml
Mouse B cells:
  PWM=0.2 to 0.02% final concentration
  LPS=2 to 5 $\mu$g/ml Cells were incubated for 3 days with PHA or ConA, or 5 days with PWM or LPS. 1 $\mu$Ci of tritiated thymidine was added to each well for the last 6 hours (or 0.5 $\mu$Ci for 18 hrs). The cells were harvested in a cell Harvester (Tortech®) and counted in a Beta counter.

For CTL activity, the data expressed is as a % augmentation compared to IL-2. IL-2 is 100%. 0 represents less than 20%, + represents 20–40%, ++ represents 40–60%, +++ represent 60–80%, and ++++ represents 80% and over.

Table 1 shows that peptide #1 (SEQ. ID NO:1) stimulates CTL's and B cells in vitro. Peptide #2 (SEQ. ID NO:2) stimulates T cells to a moderate extent and stimulates B cells. Peptide #3 (SEQ. ID NO:1) can be seen to stimulate CTL.

After in vitro drug analysis, the drugs are evaluated in whole blood for drug stability and toxicity.

TABLE 1

| Compounds | Activation of CTL/MLR | | Activation of T Cells | | Activation of B Cells | |
| --- | --- | --- | --- | --- | --- | --- |
| | CTL | MLR | ConA | PHA | LPS | PWM |
| #1 | ++($10^{-7}$M) | 0 | 0 | 0 | $1.9 - 3.6 \times (10^{-10} - 10^{-4}$ M) | $1.7 - 4 \times (10^{-6} - 10^{-4}$M) |
| #2 | ++++($10^{-9}$M) | $1.8 \times (10^{-9}$M) | $1.3 \times (10^{-12}$M $- 10^{-10}$ M) | 0 | $1.8 - 3.5 \times (10^{-8} - 10^{-5}$ M) | $1.4 - 4.5 \times (10^{-8} - 10^{-5}$ M) |
| #3 | ++($10^{-9}$M) | 0 | 0 | 0 | 0 | 0 |
| #4 | 0 | 0 | 0 | 0 | 0 | 0 |
| #5 | ++++($10^{-9}$M) | $2.1 \times (10^{-7}$M) | 0 | 0 | 0 | 0 |
| LANT-6 | +++($10^{-7}$M) | 0 | 0 | 0 | 0 | 0 |
| #6 | 0 | 0 | 0 | 0 | 0 | 0 |
| #7 | N.D. | N.D. | 0 | 0 | 0 | 0 |
| #8 | N.D. | N.D. | 0 | 0 | 0 | 0 |

N.D. = not determined

Example 3

In vivo/ex vivo Stimulation of Immune Cell Subsets

C57BL\6 mice are treated with 0, 50, 100, 200, and 300 mg/kg of drug (in saline) for 4 consecutive days. Blood is taken by cardiac puncture on day 5, and the lymphocytes are isolated from spleen in the following manner:

The spleen is aseptically removed and mashed by pressing against a steel strainer with a rubber plunger. The cell suspension is separated from the clumps by letting them settle at the bottom of the tube. The cell suspension is then separated on a Lymphocyte M layer and the interface is recovered and resuspended in media.

The following assays are performed:

1. Immunophenotyping (blood and spleen)

Cell immunophenotyping is performed on blood and spleen. The following cell surface antigens are analyzed:
CD3 (all T cells);
CD4 (T helper/inducer, binds class II-restricted T cells);
CD8 (cytotoxic T cells, CTL adhesion);
MAC-1 (monocyte/macrophage);
NK (natural killer cells);
Ly5 (CD20) (B cells);
CD45 (all leukocytes, protein tyrosine phosphatase).

Peptide #1 (SEQ. ID NO:1) was tested in one assay, the results are reported in table 1A, 2B, 3A, and 3B. In the spleen, a significant increase of relative percentage of NK+CD3+ (NK cells) and CD8+CD45+ (cytotoxic T cells) subsets was observed at 200 and 300 mg/kg for Peptide #1 (SEQ. ID NO:1).

Peptide #5 (SEQ. ID NO:1) was tested in two assays, the results of the first assay are reported in table 4A, 4B, 5A, and 5B, the results of the second assay are reported in table 6A, 6B, 7A, and 7B. On blood immunophenotyping, Peptide #5 (SEQ. ID NO:1) reduced in a significant manner the relative percentage of T cells which is shown by a reduction in TCR, CD4+ and CD8+ cell surface antigen. In a similar fashion, a significant increase of B cells is observed (Ly5 (80% CD4− CD8− (73%)) at all tested doses.

TABLE 2A

Immunophenotyping of cell subset CD45-CD4-CD8 of COMPOUND #1 in the blood

| DOSE mg/kg | CD4+ CD45− | CD4+ CD45+ | CD4− CD45− | CD4− CD45+ | CD4− CD8+ | CD4+ CD8+ | CD4− CD8− | CD4+ CD8− | CD8+ CD45− | CD8+ CD45+ | CD8− CD45− | CD8− CD45+ |
|---|---|---|---|---|---|---|---|---|---|---|---|---|
| CTL | 3.53 | 31.23 | 9.27 | 55.97 | 12.90 | 2.97 | 52.33 | 31.83 | 0.33 | 15.03 | 15.03 | 69.60 |
| (S.D.) | 0.40 | 8.89 | 3.46 | 7.43 | 6.51 | 2.25 | 15.41 | 7.01 | 0.58 | 8.49 | 3.04 | 7.20 |
| 50 | 3.80 | 26.95 | 3.90 | 65.30 | 11.20 | 3.65 | 58.05 | 27.15 | 0.55 | 13.70 | 9.60 | 76.15 |
| (S.D.) | 0.14 | 1.34 | 0.42 | 0.71 | 1.56 | 2.19 | 2.76 | 1.06 | 0.35 | 3.39 | 0.85 | 2.90 |
| P | | | | 0.28 | 0.38 | 0.10 | 0.43 | | | 0.35 | 0.04 | 0.31 |
| 100 | 8.90 | 46.75 | 7.00 | 37.30 | 11.50 | 27.20 | 32.85 | 28.55 | 6.20 | 31.95 | 14.35 | 47.55 |
| (S.D.) | 8.63 | 17.89 | 3.54 | 29.98 | 1.70 | 37.34 | 28.21 | 10.82 | 8.77 | 30.19 | 6.01 | 44.90 |
| P | | | | 0.34 | 0.39 | 0.25 | 0.32 | | | 0.31 | 0.28 | 0.36 |
| 200 | 6.22 | 33.01 | 6.74 | 40.63 | 8.57 | 16.11 | 37.41 | 24.11 | 4.13 | 20.68 | 10.39 | 49.80 |
| (S.D.) | 3.58 | 12.79 | 5.55 | 25.47 | 5.40 | 19.44 | 22.28 | 9.23 | 4.67 | 16.52 | 7.29 | 31.67 |
| P | | | | 0.44 | 0.43 | 0.25 | 0.44 | | | 0.31 | 0.43 | 0.35 |
| 300 | 2.77 | 30.67 | 4.47 | 62.10 | 16.67 | 2.37 | 49.90 | 31.07 | — | 18.10 | 8.83 | 73.03 |
| (S.D.) | 1.08 | 8.31 | 2.48 | 11.09 | 1.50 | 1.95 | 10.76 | 7.76 | — | 3.24 | 3.41 | 6.18 |
| P | | | | 0.20 | 0.19 | 0.39 | 0.42 | | | 0.31 | 0.06 | 0.17 |

TABLE 2B

Immunophenotyping of cell subset NK-CD8, B and CD4-CD11 of COMPOUND #1 in the blood

| DOSE mg/kg | NK+ CD3− | NK+ CD3+ | NK− CD3− | NK− CD3+ | Non B | B | CD4+ CD11− | CD4+ CD11+ | CD4− CD11− | CD4− CD11+ |
|---|---|---|---|---|---|---|---|---|---|---|
| CTL | 8.03 | 5.47 | 45.43 | 41.07 | 78.80 | 21.20 | 30.63 | 0.33 | 63.87 | 5.23 |
| (S.D.) | 2.50 | 5.40 | 17.50 | 9.70 | 3.98 | 3.98 | 6.21 | 0.15 | 7.52 | 1.60 |
| 50 | 10.47 | 7.83 | 40.53 | 41.23 | 76.40 | 23.57 | 34.10 | 0.53 | 57/73 | 7.67 |
| (S.D.) | 2.22 | 3.59 | 12.19 | 8.33 | 4.41 | 4.41 | 7.83 | 0.32 | 9.67 | 2.32 |
| P | 0.13 | 0.24 | | | | 0.12 | | | | |
| 100 | 6.50 | 2.80 | 53.13 | 37.57 | 80.77 | 19.23 | 41.67 | 0.23 | 55.13 | 3.00 |
| (S.D.) | 4.06 | 1.37 | 9.60 | 5.23 | 14.66 | 14.66 | 29.59 | 0.06 | 27.76 | 1.93 |
| P | 0.28 | 0.24 | | | | 0.41 | | | | |
| 200 | 8.70 | 4.57 | 55.07 | 31.73 | 79.90 | 20.10 | 39.73 | 0.50 | 54.30 | 5.50 |
| (S.D.) | 3.93 | 2.21 | 15.61 | 9.55 | 10.56 | 10.56 | 21.50 | 0.26 | 18.40 | 4.49 |
| P | 0.33 | 0.35 | | | | 0.43 | | | | |
| 300 | 11.87 | 9.97 | 35.77 | 42.43 | 66.30 | 33.67 | 29.53 | 0.37 | 65.03 | 5.07 |
| (S.D.) | 2.32 | 5.59 | 11.46 | 4.76 | 1.39 | 1.42 | 2.87 | 0.15 | 3.67 | 0.97 |
| P | 0.13 | 0.26 | | | | 0.02 | | | | |

In the blood, a significant increase of the relative percentage of B cells was observed at 300 mg/kg of compound #1

TABLE 3A

Immunophenotyping in cell subset CD45-CD4-CD8 of COMPOUND #1 in the spleen

| DOSE mg/kg | CD4+ CD45− | CD4+ CD45+ | CD4− CD45− | CD4− CD45+ | CD4− CD8+ | CD4+ CD8+ | CD4− CD8− | CD4+ CD8− | CD8+ CD45− | CD8+ CD45+ | CD8− CD45− | CD8− CD45+ | CD45-8 | CD45− Th1 |
|---|---|---|---|---|---|---|---|---|---|---|---|---|---|---|
| CTL | 4.63 | 30.47 | 1.63 | 63.33 | 11.67 | 1.97 | 53.27 | 33.10 | 0.07 | 13.03 | 7.77 | 79.17 | 62.70 | 37.35 |
| (S.D.) | 1.02 | 4.55 | 0.15 | 4.70 | 1.80 | 1.16 | 5.80 | 3.74 | 0.06 | 2.84 | 0.99 | 2.58 | 1.84 | 1.77 |
| 50 | 6.10 | 33.30 | 1.95 | 58.65 | 16.15 | 1.10 | 44.45 | 38.30 | 0.10 | 16.90 | 9.85 | 73.15 | 60.70 | 39.10 |
| (S.D.) | 0.14 | 1.27 | 0.78 | 2.33 | 1.91 | 0.14 | 0.49 | 1.56 | 0.00 | 2.12 | 1.48 | 0.64 | 1.41 | 1.41 |
| P | | | | 0.10 | | | | | | 0.16 | | | | |
| 100 | 3.80 | 30.90 | 3.85 | 61.45 | 12.45 | 2.40 | 52.85 | 32.30 | 0.05 | 14.25 | 9.35 | 76.35 | 65.55 | 34.55 |
| (S.D.) | 0.71 | 1.39 | 2.33 | 1.77 | 1.48 | 0.42 | 5.59 | 3.68 | 0.07 | 1.91 | 1.34 | 0.64 | 4.17 | 4.17 |
| P | | | | 0.33 | | | | | | 0.43 | | | | |
| 200 | 3.77 | 27.98 | 2.31 | 43.44 | 12.49 | 2.27 | 40.94 | 29.50 | 0.04 | 12.36 | 7.32 | 62.30 | 53.14 | 31.64 |
| (S.D.) | 1.55 | 12.30 | 0.81 | 29.04 | 6.16 | 1.46 | 18.14 | 13.03 | 0.04 | 8.40 | 2.96 | 30.44 | 24.16 | 13.76 |
| P | | | | 0.28 | | | | | | 0.08 | | | | |
| 300 | 3.67 | 35.00 | 3.97 | 57.40 | 16.17 | 4.33 | 45.20 | 34.30 | 0.03 | 19.77 | 10.30 | 69.93 | 61.63 | 38.43 |
| (S.D.) | 1.93 | 5.26 | 1.39 | 4.69 | 0.90 | 2.66 | 6.47 | 5.67 | 0.06 | 2.02 | 0.80 | 1.48 | 5.84 | 5.90 |
| P | | | | 0.11 | | | | | | 0.00 | | | | |

TABLE 3B

Immunophenotyping of cell subset NK-CD8,B and CD4-CD11 of COMPOUND #1 in the spleen

| DOSE mg/kg | NK+ CD3− | NK+ CD3+ | NK− CD3− | NK− CD3+ | B | CD4+ CD11− | CD4+ CD11+ | CD4− CD11− | CD4− CD11+ |
|---|---|---|---|---|---|---|---|---|---|
| CTL | 8.17 | 4.07 | 49.17 | 38.63 | 13.07 | 22.87 | 0.13 | 75.67 | 1.37 |
| (S.D.) | 0.61 | 1.88 | 10.30 | 8.80 | 1.46 | 0.80 | 0.06 | 1.11 | 0.31 |
| 50 | 7.47 | 4.70 | 45.10 | 42.80 | 11.60 | 18.47 | 0.17 | 80.17 | 1.20 |
| (S.D.) | 0.64 | 0.72 | 2.40 | 2.72 | 3.00 | 0.90 | 0.06 | 0.55 | 0.46 |
| P | 0.05 | 0.27 | 0.23 | 0.18 | 0.26 | 0.02 | | | |
| 100 | 7.93 | 4.40 | 46.20 | 41.50 | 14.97 | 18.23 | 0.20 | 80.07 | 1.53 |
| (S.D.) | 2.31 | 1.37 | 0.82 | 3.03 | 0.40 | 1.67 | 0.10 | 1.86 | 0.21 |
| P | 0.43 | 0.44 | 0.34 | 0.26 | 0.09 | 0.03 | | | |
| 200 | 8.07 | 5.27 | 42.33 | 44.33 | 16.33 | 20.03 | 0.20 | 78.27 | 1.53 |
| (S.D.) | 1.04 | 1.14 | 1.61 | 3.70 | 2.42 | 1.15 | 0.26 | 0.74 | 0.21 |
| P | 0.46 | 0.06 | 0.21 | 0.25 | 0.06 | 0.06 | | | |
| 300 | 10.83 | 9.47 | 38.63 | 41.10 | 14.60 | 20.53 | 0.53 | 76.67 | 2.23 |
| (S.D.) | 0.86 | 3.52 | 6.85 | 2.66 | 5.36 | 2.63 | 0.15 | 2.80 | 0.12 |
| p | 0.01 | 0.05 | 0.07 | 0.31 | 0.31 | 0.08 | | | |

TABLE 4A

Immunophenotyping of cell subset CD45-CD4-CD8 of COMPOUND #5 in the blood

| | CD4+ CD8− | CD4+ CD8+ | CD4− CD8− | CD4− CD8+ | CD45+ CD4− | CD45+ CD4+ | CD45− CD4− | CD45− CD4+ | CD45+ CD8− | CD45+ CD8+ | CD45− CD8− | CD45− CDE8+ |
|---|---|---|---|---|---|---|---|---|---|---|---|---|
| CTL | | | | | | | | | | | | |
| MEAN | 25.78 | 3.10 | 62.20 | 8.95 | 51.60 | 24.73 | 18.30 | 5.38 | 56.15 | 10.70 | 31.80 | 1.33 |
| S-D | 2.97 | 0.35 | 3.24 | 1.47 | 4.22 | 5.71 | 7.41 | 1.45 | 6.94 | 1.25 | 5.60 | 0.95 |
| COMPOUND #5 - 50 mg/kg | | | | | | | | | | | | |
| MEAN | 18.15 | 2.03 | 74.68 | 5.15 | 57.68 | 17.00 | 22.15 | 3.15 | 62.48 | 6.53 | 30.35 | 0.68 |
| S-D | 3.34 | 0.33 | 4.29 | 1.07 | 2.69 | 2.99 | 4.69 | 0.45 | 3.71 | 1.25 | 3.61 | 0.13 |
| P | 0.000 | 0.005 | 0.002 | 0.012 | 0.019 | 0.006 | 0.093 | 0.042 | 0.033 | 0.004 | 0.213 | 0.156 |
| COMPOUND #5 - 100 mg/kg | | | | | | | | | | | | |
| MEAN | 17.90 | 2.10 | 73.95 | 6.03 | 58.75 | 16.78 | 21.23 | 3.25 | 63.45 | 7.10 | 28.38 | 1.03 |
| S-D | 1.99 | 0.79 | 3.91 | 1.23 | 1.66 | 2.57 | 3.36 | 0.37 | 1.97 | 1.87 | 3.74 | 0.25 |
| P | 0.008 | 0.019 | 0.004 | 0.001 | 0.043 | 0.041 | 0.297 | 0.031 | 0.094 | 0.007 | 0.253 | 0.274 |
| COMPOUND #5 - 200 mg/kg | | | | | | | | | | | | |
| MEAN | 19.00 | 1.90 | 74.40 | 4.68 | 57.70 | 17.45 | 21.35 | 3.48 | 64.30 | 6.15 | 29.08 | 0.48 |
| S-D | 3.58 | 0.86 | 6.01 | 1.83 | 4.44 | 3.71 | 7.60 | 0.66 | 5.06 | 2.54 | 7.03 | 0.13 |
| P | 0.017 | 0.022 | 0.008 | 0.002 | 0.114 | 0.069 | 0.314 | 0.045 | 0.118 | 0.012 | 0.334 | 0.082 |

TABLE 4B

Immunophenotyping of cell subset NK-CD8, T.B and CD4–CD11 of COMPOUND#5 in the blood

| | NK+ CD3− | NK+ CD3+ | NK− CD3− | NK− CD3+ | TCR(T) | Ly5(B) | CD4+ CD11b− | CD4+ CD11b+ | CD4− CD11b− | CD4− CD11b+ |
|---|---|---|---|---|---|---|---|---|---|---|
| CTL | | | | | | | | | | |
| MEAN | 5.28 | 3.08 | 50.35 | 41.33 | 41.10 | 36.65 | 27.90 | 2.23 | 52.50 | 17.35 |
| S-D | 1.60 | 0.95 | 3.39 | 2.85 | 3.85 | 14.35 | 2.49 | 1.31 | 9.84 | 6.70 |
| COMPOUND #5 - 50 mg/kg | | | | | | | | | | |
| MEAN | 5.70 | 2.13 | 58.93 | 33.30 | 31.53 | 57.88 | 22.55 | 1.18 | 64.15 | 12.08 |
| S-D | 0.64 | 0.73 | 7.06 | 6.71 | 5.47 | 9.89 | 3.90 | 0.91 | 7.42 | 3.88 |
| P | 0.334 | 0.106 | 0.068 | 0.045 | 0.022 | 0.016 | 0.066 | 0.105 | 0.076 | 0.102 |
| COMPOUND #5 - 100 mg/kg | | | | | | | | | | |
| MEAN | 6.00 | 2.43 | 57.95 | 33.58 | 32.23 | 58.73 | 20.30 | 1.10 | 67.65 | 11.03 |
| S-D | 0.75 | 0.62 | 0.98 | 1.28 | 1.69 | 6.19 | 0.41 | 0.67 | 4.71 | 3.89 |
| P | 0.273 | 0.222 | 0.007 | 0.001 | 0.004 | 0.059 | 0.003 | 0.162 | 0.053 | 0.140 |
| COMPOUND #5 200 mg/kg | | | | | | | | | | |
| MEAN | 5.73 | 1.93 | 59.33 | 33.03 | 32.18 | 65.60 | 18.98 | 0.85 | 72.45 | 7.78 |

TABLE 4B-continued

Immunophenotyping of cell subset NK-CD8, T.B and CD4–CD11 of COMPOUND#5 in the blood

|     | NK + CD3− | NK + CD3+ | NK − CD3− | NK − CD3+ | TCR(T) | Ly5(B) | CD4 + CD11b− | CD4 + CD11b+ | CD4 − CD11b− | CD4 − CD11b+ |
|-----|-----------|-----------|-----------|-----------|--------|--------|--------------|--------------|--------------|--------------|
| S-D | 0.90 | 0.36 | 4.15 | 3.90 | 6.14 | 3.40 | 4.30 | 0.17 | 3.93 | 0.83 |
| P   | 0.362 | 0.023 | 0.001 | 0.007 | 0.027 | 0.014 | 0.027 | 0.063 | 0.015 | 0.028 |

TABLE 5A

Immunophenotyping of cell subset CD45-CD4-CD8 of COMPOUND #5 in the spleen

|  | CD4 + CD8− | CD4 + CD8+ | CD4 − CD8− | CD4 − CD8+ | CD45 + CD4− | CD45 + CD4+ | CD45 − CD4− | CD45 − CD4+ | CD45 + CD8− | CD45 + CD8+ | CD45 − CD8− | CD45 − CD8+ |
|--|-----------|-----------|-----------|-----------|-------------|-------------|-------------|-------------|-------------|-------------|-------------|-------------|
| CTL | | | | | | | | | | | | |
| MEAN | 33.75 | 0.60 | 59.10 | 6.53 | 55.68 | 21.75 | 8.95 | 13.65 | 66.33 | 6.10 | 26.90 | 0.68 |
| S-D | 4.56 | 0.14 | 5.14 | 0.48 | 5.14 | 3.96 | 0.48 | 0.89 | 2.73 | 0.56 | 2.12 | 0.10 |
| COMPOUND #5 - 50 mg/kg | | | | | | | | | | | | |
| MEAN | 33.05 | 0.58 | 60.65 | 5.73 | 55.25 | 21.43 | 10.03 | 13.28 | 66.00 | 5.38 | 28.05 | 0.63 |
| S-D | 1.29 | 0.05 | 1.87 | 0.68 | 1.42 | 1.21 | 1.03 | 0.68 | 1.97 | 0.51 | 1.42 | 0.17 |
| P | 0.360 | 0.380 | 0.226 | 0.015 | 0.427 | 0.430 | 0.070 | 0.029 | 0.372 | 0.016 | 0.124 | 0.302 |
| COMPOUND #5 100 mg/kg | | | | | | | | | | | | |
| MEAN | 36.85 | 0.70 | 55.50 | 7.03 | 52.10 | 23.25 | 9.30 | 15.35 | 63.43 | 6.43 | 29.30 | 0.83 |
| S-D | 1.25 | 0.26 | 1.89 | 0.54 | 1.50 | 1.58 | 0.64 | 1.18 | 1.90 | 0.82 | 1.78 | 0.05 |
| P | 0.139 | 0.177 | 0.122 | 0.050 | 0.127 | 0.222 | 0.179 | 0.054 | 0.064 | 0.189 | 0.081 | 0.007 |
| COMPOUND #5 200 mg/kg | | | | | | | | | | | | |
| MEAN | 33.73 | 0.63 | 60.00 | 5.68 | 54.03 | 21.18 | 10.48 | 14.33 | 64.83 | 5.28 | 29.35 | 0.55 |
| S-D | 2.45 | 0.13 | 3.09 | 0.56 | 3.37 | 1.60 | 1.09 | 1.00 | 2.60 | 0.62 | 2.15 | 0.06 |
| P | 0.497 | 0.427 | 0.417 | 0.085 | 0.361 | 0.421 | 0.069 | 0.262 | 0.306 | 0.111 | 0.163 | 0.071 |

TABLE 5B

Immunophenotyping of cell subset NK-CD8, T.B and CD4–CD11 of COMPOUND #5 in the spleen

|  | NK + CD3− | NK + CD3+ | NK − CD3− | NK − CD3+ | TCR(T) | Ly5(B) | CD4 + CD11b− | CD4 + CD11b+ | CD4 − CD11b− | CD4 − CD11b+ |
|--|-----------|-----------|-----------|-----------|--------|--------|--------------|--------------|--------------|--------------|
| CTL | | | | | | | | | | |
| MEAN | 3.55 | 1.68 | 57.58 | 37.20 | 38.55 | 58.53 | 25.73 | 0.78 | 70.13 | 3.40 |
| S-D | 0.17 | 0.21 | 3.51 | 3.40 | 3.14 | 3.91 | 2.04 | 0.05 | 2.60 | 0.71 |
| COMPOUND #5 50 mg/kg | | | | | | | | | | |
| MEAN | 3.78 | 1.50 | 56.68 | 38.13 | 40.23 | 57.85 | 23.88 | 0.83 | 71.73 | 3.63 |
| S-D | 0.28 | 0.18 | 1.19 | 1.40 | 1.10 | 1.69 | 0.70 | 0.10 | 0.88 | 0.24 |
| P | 0.039 | 0.094 | 0.325 | 0.326 | 0.199 | 0.380 | 0.044 | 0.196 | 0.117 | 0.292 |
| COMPOUND #5 100 mg/kg | | | | | | | | | | |
| MEAN | 3.88 | 1.83 | 55.95 | 38.38 | 39.83 | 56.75 | 23.73 | 0.95 | 71.23 | 4.10 |
| S-D | 0.32 | 0.13 | 1.62 | 1.51 | 1.90 | 1.47 | 1.25 | 0.06 | 1.33 | 0.34 |
| P | 0.137 | 0.091 | 0.124 | 0.217 | 0.190 | 0.160 | 0.020 | 0.018 | 0.096 | 0.094 |
| COMPOUND #5 200 mg/kg | | | | | | | | | | |
| MEAN | 3.88 | 1.95 | 58.50 | 35.70 | 37.30 | 59.50 | 22.65 | 1.00 | 72.00 | 3.58 |
| S-D | 0.22 | 0.25 | 2.23 | 2.27 | 1.94 | 1.49 | 1.31 | 0.22 | 1.54 | 0.28 |
| P | 0.016 | 0.112 | 0.379 | 0.303 | 0.313 | 0.370 | 0.071 | 0.068 | 0.129 | 0.285 |

TABLE 6A

Immunophenotyping of cell subset CD45-CD4-CD8 of COMPOUND #5 in the blood

|  | CD4 + CD8− | CD4 + CD8+ | CD4 − CD8− | CD4 − CD8+ | CD45 + CD4− | CD45 + CD4+ | CD45 − CD4− | CD45 − CD4+ | CD45 + CD8− | CD45 + CD8+ | CD45 − CD8− | CD45 − CD8+ |
|--|-----------|-----------|-----------|-----------|-------------|-------------|-------------|-------------|-------------|-------------|-------------|-------------|
| CTL | | | | | | | | | | | | |
| MEAN | 25.85 | 0.58 | 62.70 | 7.23 | 65.80 | 24.45 | 8.00 | 1.78 | 83.45 | 7.73 | 8.75 | 0.08 |
| S-D | 2.25 | 0.13 | 3.15 | 2.11 | 4.78 | 1.95 | 3.09 | 0.38 | 3.04 | 2.20 | 3.33 | 0.05 |

TABLE 6A-continued

Immunophenotyping of cell subset CD45-CD4-CD8 of COMPOUND #5 in the blood

| | CD4 + CD8− | CD4 + CD8+ | CD4 − CD8− | CD4 − CD8+ | CD45 + CD4− | CD45 + CD4+ | CD45 − CD4− | CD45 − CD4+ | CD45 + CD8− | CD45 + CD8+ | CD45 − CD8− | CD45 − CD8+ |
|---|---|---|---|---|---|---|---|---|---|---|---|---|
| COMPOUND #5 - 50 mg/kg | | | | | | | | | | | | |
| MEAN | 20.65 | 0.43 | 71.20 | 7.70 | 68.23 | 18.48 | 11.05 | 2.25 | 79.70 | 8.10 | 12.15 | 0.03 |
| S-D | 2.38 | 0.15 | 2.46 | 1.41 | 5.37 | 2.46 | 6.42 | 0.47 | 5.58 | 1.54 | 6.28 | 0.05 |
| P | 0.025 | 0.148 | 0.017 | 0.383 | 0.306 | 0.014 | 0.219 | 0.157 | 0.127 | 0.413 | 0.206 | 0.091 |
| COMPOUND #5 - 100 mg/kg | | | | | | | | | | | | |
| MEAN | 25.00 | 0.33 | 67.83 | 6.80 | 68.45 | 22.70 | 6.63 | 2.23 | 85.00 | 7.05 | 7.83 | 0.10 |
| S-D | 5.57 | 0.21 | 6.91 | 1.93 | 7.19 | 5.09 | 2.35 | 0.49 | 4.58 | 2.09 | 2.52 | 0.08 |
| P | 0.413 | 0.078 | 0.390 | 0.397 | 0.335 | 0.314 | 0.286 | 0.186 | 0.345 | 0.352 | 0.365 | 0.196 |
| COMPOUND #5 200 mg/kg | | | | | | | | | | | | |
| MEAN | 23.13 | 0.30 | 69.03 | 7.58 | 71.95 | 20.85 | 5.00 | 2.23 | 85.60 | 7.83 | 6.53 | 0.05 |
| S-D | 4.28 | 0.08 | 4.80 | 0.82 | 5.51 | 4.32 | 1.34 | 0.35 | 1.61 | 0.88 | 1.34 | 0.06 |
| P | 0.205 | 0.011 | 0.229 | 0.330 | 0.093 | 0.140 | 0.053 | 0.007 | 0.111 | 0.451 | 0.099 | 0.319 |

TABLE 6B

Immunophenotyping of cell subset NK-CD8, T.B and CD4–CD11 of COMPOUND #5 in the blood

| | NK + CD3− | NK + CD3+ | NK − CD3− | NK − CD3+ | TCR(T) | Ly5(B) | CD4 + CD11b− | CD4 + CD11b+ | CD4 − CD11b− | CD4 − CD11b+ |
|---|---|---|---|---|---|---|---|---|---|---|
| CTL | | | | | | | | | | |
| MEAN | 7.05 | 3.58 | 50.43 | 38.95 | 42.33 | 54.65 | 18.20 | 0.23 | 74.30 | 7.28 |
| S-D | 0.55 | 0.68 | 4.29 | 4.60 | 5.34 | 2.73 | 4.23 | 0.13 | 5.52 | 1.53 |
| COMPOUND #5 50 mg/kg | | | | | | | | | | |
| MEAN | 7.88 | 3.00 | 58.10 | 31.05 | 35.73 | 58.6 | 15.38 | 0.13 | 77.78 | 6.73 |
| S-D | 0.82 | 0.41 | 3.11 | 3.20 | 3.38 | 3.77 | 1.44 | 0.05 | 2.63 | 1.92 |
| P | 0.057 | 0.043 | 0.028 | 0.023 | 0.033 | 0.101 | 0.191 | 0.046 | 0.198 | 0.357 |
| COMPOUND #5 100 mg/kg | | | | | | | | | | |
| MEAN | 7.58 | 4.68 | 51.43 | 36.30 | 37.50 | 56.10 | 21.58 | 0.50 | 67.65 | 10.28 |
| S-D | 1.49 | 2.32 | 13.87 | 10.49 | 10.52 | 15.70 | 7.72 | 0.54 | 13.39 | 5.22 |
| P | 0.305 | 0.155 | 0.453 | 0.358 | 0.269 | 0.438 | 0.220 | 0.144 | 0.179 | 0.129 |
| COMPOUND #5 200 mg/kg | | | | | | | | | | |
| MEAN | 6.83 | 2.90 | 58.03 | 32.30 | 35.80 | 65.63 | 15.40 | 0.13 | 79.30 | 5.20 |
| S-D | 0.42 | 0.14 | 4.13 | 4.37 | 2.86 | 5.36 | 4.67 | 0.05 | 5.25 | 0.91 |
| P | 0.326 | 0.052 | 0.036 | 0.060 | 0.073 | 0.029 | 0.230 | 0.126 | 0.160 | 0.071 |

TABLE 7A

Immunophenotyping of cell subset CD45-CD4-CD8 of COMPOUND #5 in the spleen

| | CD4 + CD8− | CD4 + CD8+ | CD4 − CD8− | CD4 − CD8+ | CD45 + CD4− | CD45 + CD4+ | CD45 − CD4− | CD45 − CD4+ | CD45 + CD8− | CD45 + CD8+ | CD45 − CD8− | CD45 − CD8+ |
|---|---|---|---|---|---|---|---|---|---|---|---|---|
| CTL | | | | | | | | | | | | |
| MEAN | 37.38 | 0.50 | 56.95 | 5.23 | 51.70 | 30.05 | 9.55 | 8.65 | 78.45 | 5.33 | 16.08 | 0.13 |
| S-D | 1.42 | 0.14 | 1.79 | 1.08 | 1.85 | 1.56 | 2.66 | 0.57 | 2.24 | 1.03 | 2.74 | 0.05 |
| COMPOUND #5 50 mg/kg | | | | | | | | | | | | |
| MEAN | 36.53 | 0.63 | 57.03 | 5.85 | 49.85 | 29.23 | 12.05 | 8.83 | 75.15 | 6.03 | 18.65 | 0.18 |
| S-D | 5.17 | 0.25 | 5.79 | 0.93 | 3.12 | 4.10 | 6.62 | 0.93 | 5.40 | 0.78 | 5.95 | 0.05 |
| P | 0.358 | 0.171 | 0.488 | 0.151 | 0.203 | 0.330 | 0.210 | 0.380 | 0.100 | 0.108 | 0.185 | 0.091 |
| COMPOUND #5 100 mg/kg | | | | | | | | | | | | |
| MEAN | 31.78 | 0.53 | 63.03 | 4.68 | 50.20 | 26.40 | 16.60 | 6.83 | 73.48 | 4.80 | 21.68 | 0.10 |
| S-D | 2.71 | 0.05 | 3.53 | 0.94 | 5.73 | 2.17 | 8.27 | 0.94 | 7.13 | 0.92 | 7.95 | 0.08 |
| P | 0.015 | 0.359 | 0.015 | 0.130 | 0.303 | 0.023 | 0.086 | 0.037 | 0.131 | 0.130 | 0.120 | 0.359 |
| COMPOUND #5 200 mg/kg | | | | | | | | | | | | |
| MEAN | 36.13 | 0.55 | 58.40 | 4.95 | 52.45 | 29.00 | 9.98 | 8.63 | 78.23 | 5.08 | 16.60 | 0.13 |

TABLE 7A-continued

Immunophenotyping of cell subset CD45-CD4-CD8 of COMPOUND #5 in the spleen

|     | CD4 + CD8− | CD4 + CD8+ | CD4 − CD8− | CD4 − CD8+ | CD45 + CD4− | CD45 + CD4+ | CD45 − CD4− | CD45 − CD4+ | CD45 + CD8− | CD45 − CD8+ | CD45 − CD8− | CD45 − CD8+ |
|-----|------------|------------|------------|------------|-------------|-------------|-------------|-------------|-------------|-------------|-------------|-------------|
| S-D | 4.71       | 0.13       | 5.32       | 0.77       | 1.87        | 4.39        | 3.11        | 0.86        | 2.47        | 0.78        | 2.91        | 0.05        |
| P   | 0.346      | 0.319      | 0.332      | 0.365      | 0.314       | 0.360       | 0.426       | 0.484       | 0.453       | 0.377       | 0.411       | 0.500       |

TABLE 7B

Immunophenotyping of cell subset NK-CD8, T.B and CD4–CD11 of COMPOUND #5 in the spleen

|  | NK + CD3− | NK + CD3+ | NK − CD3− | NK − CD3+ | TCR(T) | Ly5(B) | CD4 + CD11b− | CD4 + CD11b+ | CD4 − CD11b− | CD4 − CD11b+ |
|---|---|---|---|---|---|---|---|---|---|---|
| CTL | | | | | | | | | | |
| MEAN | 3.43 | 1.73 | 54.33 | 40.55 | 54.18 | 39.25 | 17.65 | 0.28 | 78.15 | 3.93 |
| S-D | 0.53 | 0.22 | 3.27 | 3.86 | 4.81 | 5.06 | 2.78 | 0.05 | 2.60 | 0.64 |
| COMPOUND #5 50 mg/kg | | | | | | | | | | |
| MEAN | 3.83 | 2.18 | 54.38 | 39.60 | 51.58 | 41.20 | 14.85 | 0.38 | 81.15 | 3.60 |
| S-D | 0.33 | 0.34 | 5.08 | 5.22 | 5.63 | 3.11 | 2.15 | 0.05 | 2.43 | 0.47 |
| P | 0.180 | 0.0007 | 0.489 | 0.273 | 0.249 | 0.283 | 0.159 | 0.000 | 0.155 | 0.176 |
| COMPOUND #5 100 mg/kg | | | | | | | | | | |
| MEAN | 4.10 | 2.25 | 65.05 | 28.65 | 40.33 | 48.28 | 14.65 | 0.33 | 81.53 | 3.53 |
| S-D | 0.80 | 0.31 | 4.04 | 3.35 | 2.05 | 2.88 | 0.87 | 0.10 | 1.51 | 0.81 |
| P | 0.079 | 0.063 | 0.013 | 0.012 | 0.007 | 0.038 | 0.088 | 0.248 | 0.092 | 0.222 |
| COMPOUND #5 200 mg/kg | | | | | | | | | | |
| MEAN | 4.35 | 2.35 | 61.10 | 32.15 | 47.23 | 46.50 | 13.10 | 0.33 | 78.38 | 3.20 |
| S-D | 0.56 | 0.54 | 5.04 | 4.23 | 5.78 | 5.15 | 2.51 | 0.05 | 9.55 | 0.39 |
| P | 0.050 | 0.076 | 0.045 | 0.032 | 0.041 | 0.012 | 0.076 | 0.196 | 0.481 | 0.046 |

2. Mitogenic proliferation of T and B cells (spleen)

Figure 1B:
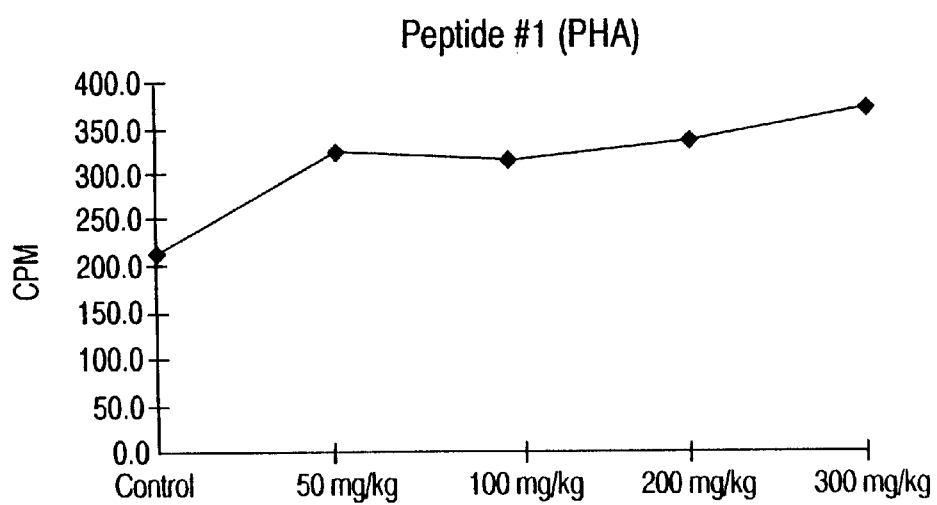
Figure 1C:
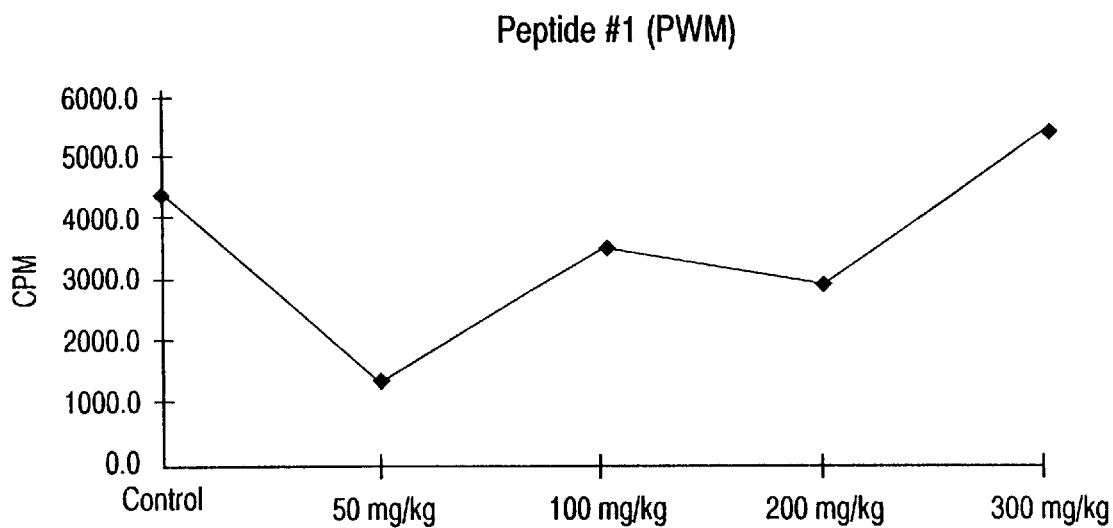
Figure 1D:
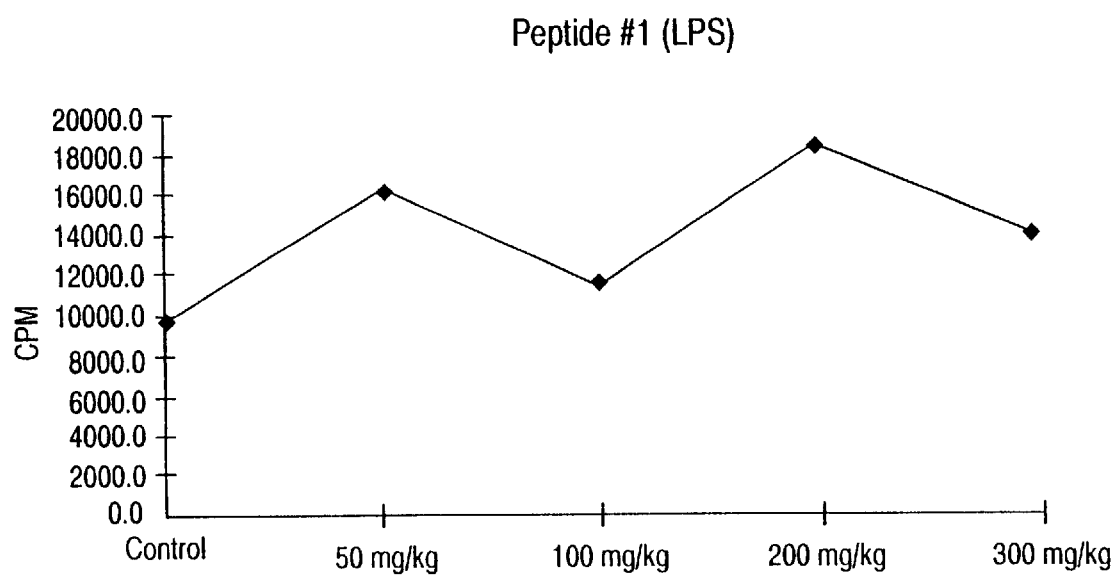

Peptide #1 (SEQ. ID NO:1) is also shown to activate T and B cells in spleen in vivo/ex vivo (see FIGS. 1A, 1B, 1C and 1D).

3. NK assay

Important in immunosurveillance, NK cells are capable of lysing tumors, virus-infected or embryo-derived cells in vitro spontaneously without prior sensitization. Immunomodulators are evaluated using murine splenocytes and human peripheral blood mononuclear leukocytes.

Spleen cells were used to test for NK activity at a effector:target ratio of 100:1.

TABLE 8

Functional in vivo/ex vivo NK cell assay of Peptide #1 (SEQ. ID NO:1) in mice.

| Group | Average | S.D. | % response of IL-2 | % response of CTL |
|---|---|---|---|---|
| Control | 2.42 | 0.69 | 42.98 | 100.00 |
| IL-2 | 5.22 | — | 100.00 | 233.04 |
| 50 mg/kg | 2.52 | 0.11 | 48.34 | 112.48 |
| 100 mg/kg | 3.63 | 0.94 | 69.48 | 161.66 |
| 200 mg/kg | 2.77 | 0.74 | 53.13 | 123.63 |
| 300 mg/kg | 3.05 | 0.11 | 58.49 | 136.11 |

EXAMPLE 4

Toxicity peptide #1 (SEQ. ID NO:1) appears to be non-toxic. No apparent toxicity was observed in vivo when animals were treated with 50, 100, 200, and 300 mg/kg of the peptide.

No toxic effect was recorded for peptide #5 (SEQ. ID NO:1) up to 200 mg/kg. Gross pathological observations demonstrated no sign of irritation.

Example 5

Stability of peptide #5 (SEQ. ID NO:1) in Rat Whole Blood at 37° C.

METHOD

1. ANALYTICAL PROCEDURE

Column: YMC phenyl, 3 mm, 120 A°, 4.6×150 mm
Flow Rate: 0.5 ml/minute
Activation: 205 nm
Eluent: A=$CH_3CN$ B=Ammonium Acetate 0.01 M pH 6
Program: 0–5 minutes 5% A/B 5–25 minutes 5%→15% A/B Curve 6 25–30 minutes 15%→50% A/B Curve 6
Attenuation: 0.3 AU
Injection: 30 ml

2. BLOOD INCUBATION

Stock solution of the peptide is prepared at a concentration of 1.1mg/ml and dissolved in 10% $CH_3CN/H_2O$.

Rat Whole Blood (EDTA) is spiked with the peptide to give a concentration of 55 mg/ml.

Same concentration of 10% $CH_3CN/H_2O$ is also spiked to Rat Whole Blood (EDTA) as a control blank.

Aliquotes of 500ml are taken (in duplicate) of both spiked and control blanks at the following times:

FOR SPIKED BLOOD: 0', 5', 10', 15', 30', 45', 60', 75', 90'.

FOR BLANK BLOOD: 0', 90'.

Each aliquoted samples are centrifuged at 4° C., 4400 rpm for 10 minutes.

23

3. Extraction Procedure: Liquid—Liquid Extraction Protein Precipitation

For each plasma sample, 100 μl of plasma are transferred to an eppendorf vial and 200 μl of acetonitrile added to it. The mixture is vortexed for 30 seconds and centrifuged at 4° C., 5 minutes 14000 rpm (Centra MP4R centrifuge, rotor # IEC 851). 200 μl of supernatant are transferred to another vial and evaporated to dryness with the Speed vac Plus (Savant SC-110A). The dried sample is reconstituted with 100 ml of Mobile phase and an aliquote of this is injected to HPLC(high pressure liquid chromatography) for analysis.

Results

The results of the HPLC analysis are presenred on Table 9.

1. peptide #5 (SEQ. ID NO:1) has a preliminary Extraction Efficiency of 69%±7%.
2. peptide #5(SEQ. ID NO:1) has a half life in Rat Whole Blood>90 minutes.

TABLE 9

| Time (Min.) | Area |
| --- | --- |
| 0 | 2471958 |
| 5 | 2362251.2 |
| 10 | 2386700 |
| 15 | 2965610 |
| 30 | 2038700.5 |
| 45 | 2186985.5 |
| 60 | 2194185.5 |
| 75 | 2559208.5 |
| 90 | 2263081.5 |

Example 6

Stability of Peptide #1 (SEQ. ID. NO:1) and Peptide #5(SEQ. ID NO:1) in Human Whole Blood at 37° C.

The procedures are the same as example 5 with the exceptions that human whole blood was substituted for rat whole blood, and that in Step 2, (blood incubation) aliquotes were taken at the following times:

24

FOR SPIKED BLOOD: 0', 15', 30', 60', 90', 120', 150'180' and 210'.

FOR BLANK BLOOD: 0', 60', 180', 210.

RESULTS

Thr results of the HPLC analysis are presented on Table 10.

1. peptide #1 (SEQ. ID NO:1) has a half life in Human Whole Blood (37° C.)~20 min.
2. peptide #5 (SEQ. ID NO:1) has a half life in Human Whole Blood (37° C.)>210 min.

TABLE 10

| Time (Min.) | PEPTIDE #1 (SEQ. ID NO:1) AREA | PEPTIDE #5 (SEQ. ID NO:1) |
| --- | --- | --- |
| 0 | 887657 | 2857082.5 |
| 15 | 354842 | 3066465 |
| 30 | 127725 | 3017509.5 |
| 45 | 0 | — |
| 60 | — | 3135696.5 |
| 90 | — | 3005211 |
| 120 | — | 3476665.5 |
| 150 | — | 3063052 |
| 180 | — | 3108157 |
| 210 | — | 3181899 |

We claim:

1. A peptide of the formula (I):

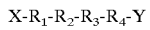

wherein;

X is selected from the group consisting of H or acetyl;

$R_1$ is selected from the group consisting of D or L-lysine; arginine; ornithine and histidine;

$R_2$ is selected from the group consisting of D or L-asparagine; alanine; proline; glutamine; serine; threonine; and valine;

$R_3$ is selected from the group consisting of D or L-proline; alanine; asparagine; glutamine; serine; threonine; valine; and glycine;

$R_4$ is selected from the group consisting of D or L-tyrosine; cysteine; serine; threonine; phenylalanine; tryptophan; and histidine; and Y is selected from the group consisting of OH, $NH_2$, and $OC_{1-6}$ alkyl.

2. The peptide according to claim 1 wherein X is hydrogen.

3. The peptide according to claim 1 wherein $R_1$ is D-lysine.

4. The peptide according to claim 1 wherein $R_2$ asparagine.

5. The peptide according to claim 1 wherein $R_2$ is glutamine.

6. The peptide according to claim 1 wherein $R_3$ is D-Proline.

7. The peptide according to claim 1 wherein $R_4$ is tyrosine.

8. The peptide according to claim 1 wherein $R_4$ is phenylalanine.

9. The peptide according to claim 1 wherein Y is OH.

10. A pharmaceutical composition containing a peptide according to claim 1, wherein said peptide is present in admixture with a pharmaceutically acceptable carrier.

11. The pharmaceutical composition according to claim 10 wherein peptide is present in admixture with another therapeutically active agent.

12. A method for the treatment of immune deficiencies comprising the step of administering to a mammal, including human, a pharmaceutically acceptable amount of a peptide according to claim 1.

13. A method for stimulating B-cells comprising the step of administering to a mammal, including human, a pharmaceutically acceptable amount of a peptide according to claim 1.

14. The method according to claim 13, wherein said peptide is administered in an amount ranging from about 0.1 to about 750 mg/kg.

15. A method of manufacturing a medicament for the treatment of immune deficiencies, using a peptide according to claim 1, in an amount effective to produce an immune response.

16. A peptide selected from the group consisting of:

peptide #1 H-Lys-Asn-Pro-Tyr-OH (SEQ ID NO:1);

peptide #2 H-Lys-Asn-Gly-Tyr-OH (SEQ ID NO:2);

peptide #3 H-Lys-Asn-(D-Pro)-Tyr-OH (SEQ ID NO:1);

peptide #4 H-Lys-Asn-Pro-Phe-OH (SEQ ID NO:3);

peptide #5 H-(D-Lys)-Asn-Pro-Tyr-OH (SEQ ID NO:1);

peptide #6 H-Lys-Gln-Pro-Tyr-OH (SEQ ID NO:4);

peptide #8 H-Gly-Asn-Pro-Tyr-OH (SEQ ID NO:6);

peptide #9 H-(D-Lys)-Asn-Gly-Tyr-OH (SEQ ID NO:2);

peptide #10 H-(D-Lys)-Gln-Pro-Tyr-OH (SEQ ID NO:4); and peptide #11 H-(D-Lys)-Asn-Pro-Phe-OH (SEQ ID NO:3).

17. The peptide according to claim 16 selected from the group consisting of:

peptide #1 (SEQ. ID NO:1) H-Lys-Asn-Pro-Tyr-OH; (SEQ. ID NO:1) and peptide #5 H-(D-Lys)-Asn-Pro-Tyr-OH (SEQ. ID NO:1).

18. The peptide according to claim 17 of the formula:

peptide #1 H-Lys-Asn-Pro-Tyr-OR (SEQ. ID NO:1).

19. The peptide according to claim 17 of the formula:

peptide #5 H-(D-Lys)-Asn-Pro-Tyr-OH (SEQ. ID NO:1).

* * * * *